United States Patent [19]

Craig et al.

[11] 4,292,029
[45] Sep. 29, 1981

[54] HYDROPHOBIC COMPOSITE RESTORATIVE MATERIALS AND THEIR USE IN TOOTH TREATMENT

[75] Inventors: Robert G. Craig, Ann Arbor, Mich.; William H. Douglas, Cardiff, England

[73] Assignee: University of Michigan, Ann Arbor, Mich.

[21] Appl. No.: 72,676

[22] Filed: Sep. 5, 1979

Related U.S. Application Data

[63] Continuation-in-part of Ser. No. 905,936, May 15, 1978, abandoned.

[51] Int. Cl.$^3$ ............................................... A61K 5/06
[52] U.S. Cl. ................................. 433/228; 260/42.49; 525/276; 526/329.4
[58] Field of Search ......................... 32/15; 260/42.49; 526/329.4; 433/228

[56] References Cited

U.S. PATENT DOCUMENTS

| | | | |
|---|---|---|---|
| 3,066,112 | 11/1962 | Bowen | 260/41 |
| 3,082,526 | 3/1963 | Nitzacke et al. | 32/15 |
| 3,179,623 | 4/1965 | Bowen | 260/47 |
| 3,469,317 | 9/1969 | Jarby | 32/15 |
| 3,539,533 | 11/1970 | Lee et al. | 260/47 |
| 3,540,126 | 11/1970 | Chang et al. | 32/15 |
| 3,730,947 | 5/1973 | Stoffey et al. | 260/47 U A |
| 3,751,399 | 8/1973 | Lee et al. | 260/47 U A |
| 3,766,132 | 10/1973 | Lee et al. | 260/41 A |
| 3,825,518 | 7/1974 | Sheerniss et al. | 260/42.52 |
| 3,882,600 | 5/1975 | Plymale | 32/15 |
| 3,925,895 | 12/1975 | Kliment et al. | 32/15 |
| 3,997,504 | 12/1976 | Plymale | 260/42.27 |
| 4,107,845 | 8/1978 | Lee et al. | 32/15 |

OTHER PUBLICATIONS

Overberger et al. (J. Pol. Sci. A-1,13; 1782-1792, 1975).
O'Brien et al. (J. Colloid & Interface Sci., 26 500-508, 1968).
Brauer et al. (J. Biomed. Mat. Res. 13: 593-606, 1979).
Leonard (Annals New York Academy of Sci., 146: 203-213, 1968).
Beech (J. Dent. Res., 51: 1438-1442, 1972).
Craig et al. (AADR Abstracts, #657 p. B216, Jun. 1977).
Douglas et al. (IADR Abstracts, #703, p. 250, 1978).
Antonucci et al., (IADR Abstracts, #599, p. 242, 1979).

*Primary Examiner*—Carman J. Seccuro

[57] ABSTRACT

Penetration of fluids between a tooth and a restoration is prevented, without chemical adhesive of the restorative material to the tooth by forming the restoration from a dental composition which is hydrophobic to the extent that the advancing contact angle of water or saliva on the restorative material is at least about 130°. The hydrophobic nature of the contoured surface of the composite also minimizes staining by soluble dyes and accretion of hydrophilic gelatinous surface films.

10 Claims, No Drawings

HYDROPHOBIC COMPOSITE RESTORATIVE MATERIALS AND THEIR USE IN TOOTH TREATMENT

This application is a continuation-in-part of application Ser. No. 905,936, filed May 15, 1978, now abandoned.

BACKGROUND OF THE INVENTION

This invention relates to the use of dental compositions which exhibit an advancing contact angle of at least about 130° relative to saliva, and in particular, to the use of dental filling composite materials comprised of a finely divided, inert inorganic filler and a hydrophobic binder system. The distinctive features attributable to the use of such dental compositions include the formation of restorations which, in relation to water, exhibit a low wettability, a high contact angle, a low absorption of water at equilibrium, a relatively high diffusion coefficient for water and ionic species, and a free surface energy change, $\Delta F$, which is positive.

An equation which describes the driving force for penetration of a liquid into a capillary space has been developed by O'Brien et al (J. Colloid & Interface Science, 26: 500 508, 1968). The equation relates the free surface energy change, $\Delta F$, to the surface tension of the liquid, $\gamma_{1v}$ and the contact angles of the liquid against tooth structure, $\theta_1$, and the restorative material, $\theta_2$. The equation is as follows:

$$-\Delta F = \gamma_{1v}(\cos\theta_1 + \cos\theta_2)$$

If $\Delta F$ is negative, then penetration of the liquid is spontaneous; whereas, if $\Delta F$ is positive, outside pressure must be applied to force liquid into the capillary space.

The use of acrylic resins as binders in dental filling composites is disclosed for example, in detail in U.S. Pat. No. 3,066,112 to Bowen; U.S. Pat. No. 3,179,623 to Bowen; U.S. Pat. No. 3,539,533 to Lee, II et al; U.S. Pat. No. 3,540,126 to Chaug et al; U.S. Pat. No. 3,751,399 to Lee, Jr., et al; and U.S. Pat. No. 3,825,518 to Foster et al.

While such prior art acrylate resin compositions have been proven useful, it is known that many such compositions exhibit only limited resistance to wettability by water, and thus permit penetration or microleakage of saliva and other aqueous fluids at the margins of a restoration. Some of the compositions, for example, the fluoroalkoxyalkyl-2-cyanoacrylates disclosed in the above patent to Chaug et al are somewhat hydrolyzable and, therefore, biodegradable. Accordingly, while such materials are described as being useful as sealants, adhesives and coatings in the art of dentistry and medicine, these materials tend to be even more readily degradable in the mouth than the alkyl types of acrylate resins. Thus, even though the Chaug et al compositions might exhibit significant adhesion and bond strength to tooth structure, the bond strength will degrade with time, thus allowing penetration or microleakage of saliva and other aqueous fluids at the boundaries between the tooth and the fluoroalkoxyalkyl-2-cyanoacrylate composition.

The advancing contact angle of water on a fluorinated cyanoacrylate of the type described in the patent by Chaug et al is considerably lower than 130°. For example, the advancing contact angle of water on Flucrylate cyanoacrylate, a fluorinated cyanoacrylate of the Chaug et al type obtainable from the Surgical Products Division of the Minnesota Mining and Manufacturing Co., is 97°±3°.

The degradation of the bond strength of cyanoacrylates to bone has been demonstrated by Brauer et al (J. Biomed. Mat. Res. 13:593–606, 1979). Thus, the bond strength of isobutyl 2-cyanoacrylate decreased from 6.6 MPa to 2.0 MPa after six months storage in water, and the bond strength with the ethyl derivative decreased from 6.6 MPa to 0.2 MPa in one month. The bond strength at one day for fluorinated 2-cyanoacrylate was 1.1 MPa. Earlier studies by Leonard (Annals New York Academy Science 146:203–213, 1968) and Beech (J. Dent. Res. 51:1438–1442, 1972) demonstrated the degradation of cyanoacrylates in vivo and in vitro with bond strengths decreasing 50% in seven days in water.

It is known that microleakage is one of the main etiologic factors in recurrent caries. Further, the ready accretion of plaque onto the contoured surfaces of such materials places the health of contiguous gingival tissues at risk, and reduces the aesthetic values of restorations due to a predisposition to staining.

SUMMARY OF THE INVENTION

Accordingly, it is a primary object of the present invention to treat teeth with a hydrophobic dental restorative composition which exhibits in relation to water, a low wettability, a high contact angle, a relatively high diffusion coefficient for water and ionic species, a low absorption at equilibrium, and which exhibit, in relation to prior art dental compositions, favorable working properties, physical properties, resiliency, wear resistance, and stain resistance.

It is another object to provide a process for restoring teeth by using a dental composition which exhibits a high degree of resistance to marginal leakage, without having to resort to the bond strength or chemical adhesion between the tooth and the dental composition to achieve the desired results.

Another object of the invention is to use as a dental restorative composition a hydrophobic resin system which, even in the presence of a capillary space between a tooth and the restoration, will inhibit leakage into the capillary space by virtue of the hydrophobic character of the restorative composition, and not the adhesive or bond strength characteristics thereof.

Another object is to use a dental restorative composition which is hydrophobic such that the sum of the free surface energy changes as a result of saliva wetting the tooth and the restoration is positive.

Still another object is to provide a dental composition which exhibits a hydrophobic character that will minimize the adsorption and retention of stains and organic films on the anatomical contoured surfaces exposed to saliva.

Yet another object is to provide hydrophobic dental filling compositions which can be packaged as either one-paste or two-paste systems for convenient handling characteristics.

Another object is to provide hydrophobic dental compositions which can be molded at ambient temperatures under digital pressure, which exhibit very satisfactory gel and set times, high compressive and flexural strengths, low degrees of shrinkage on cure, and low coefficients of thermal expansion.

Yet another object is to provide a hydrophobic dental composition which can be pressed into enamel surfaces roughened by standard acid etching techniques such that the tags of material extending into enamel provide mechanical retention of the restoration.

It has now been found that these and other objects and advantages can be obtained in accordance with the present invention by applying to a cavity preparation and tooth surface a composition comprising a mixture of from about 10-90% by weight of a finely divided, inert inorganic filler and from about 90-10% by weight of hydrophobic binder system, and polymerizing the composition thereon.

Strictly speaking, whether a given material or binder system is hydrophilic or hydrophobic in relation to water or saliva depends upon whether the contact angle $\theta$, particularly the advancing contact angle $\theta_A$, of a drop of the liquid placed on the material is lesser or greater than 90°, with those materials exhibiting a contact angle of greater than $\theta = 90°$ being hydrophobic. However, there are varying degrees of hydrophilicity and hydrophobicity, and not all dental composite materials exhibiting a contact angle, in relation to water of greater than 90°, can be used to achieve the desired results of the present invention. Rather, it has now been found that penetration of fluids between the tooth and a restoration may be prevented without resort to chemical adhesion if the wettability of the surfaces of the tooth and restoration are such that the sum of the cosines of the advancing contact angles of the fluid against the tooth and restoration is negative; under these conditions the free energy change, $\Delta F$, will be positive. Thus, since the contact angle, $\theta_A$, for teeth is about 55°, the advancing contact angle, $\theta_A$, of the restoration must be greater than about 130° and, preferably, greater than about 140° to provide the desired results. Accordingly, as used in the specification and claims, the term "hydrophobic" is used to describe only materials which exhibit an advancing contact angle, $\theta_A$, in relation to saliva or water of at least about 130° and, preferably, at least about 140°.

Bearing the foregoing in mind, the hydrophobic systems which may be used in the present process comprise either (1) a polymerizable prepolymer system containing at least one fluorine-containing prepolymer, wherein all of the prepolymers in the system, if more than one prepolymer is employed, are mutually soluble before and after polymerization, or (2) a particulate fluorine-containing polymer which is dispersed in a second prepolymer system which may be the same or different from (1). As used herein, the term "prepolymer" is meant to describe monomers as well as oligomers and "prepolymer system" is meant to describe a mixture comprising one or more monomers and/or oligomers and/or mixtures thereof.

It will be understood, of course, that regardless of whether the binder system is comprised of a particulate fluorine-containing polymer, a polymerizable prepolymer system or a mixture thereof, the binder system, when fully polymerized in the presence of the inorganic filler, must be sufficiently hydrophobic to exhibit an advancing contact angle of at least about 130° and, preferably, at least about 140°.

When the binder system comprises a polymerizable fluorine-containing prepolymer system, the monomer(s) and/or oligomer(s) suitable for preparing the system must be mutually soluble as monomers and/or oligomers, and still must be soluble after polymerization has taken place. This can be achieved by using fluorine-containing analogues of most or all of the acrylate monomers and/or oligomers conventionally employed in dental resins. For example, there may be used fluorine analogues of Bisphenol adducts of methacrylate, commonly called Bisphenol F, and fluorine analogues of the adducts of nonaromatic di- and tri-hydric alcohols and methacrylate, such as, tetrafluoroethyleneglycol dimethacrylate. Still other fluorine-containing materials which may be used to prepare the prepolymers include:

perfluoroalkyl acrylate monomers, such as tetrafluoropropyl methacrylate, pentafluorophenyl methacrylate, hexafluorohexyl methacrylate, hexafluoroisopropyl methacrylate, and octafluoropentyl methacrylate;

dimethacrylates, such as fluorinated analogues of mono-, di-, tri-, and tetra-ethylene glycol dimethacrylates;

aromatic dimethacrylates, such as
(1) Bisphenol A adducts of methacrylates in which alkyl groups are fluorinated,
(2) Bisphenol A adducts in which aromatic groups are fluorinated, and
(3) Bisphenol A adducts in which the aromatic and methacrylate groups are fluorinated.

Other unsaturated molecules which can be used include, for example,
fluorovinyl toluene,
fluorostyrene, and
fluoroalkyl methacrylate, as well as
fluorinated acrylates of the following types:

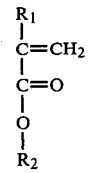

where $R_1$ is a $C_1-C_4$ alkyl group and $R_2$ is a fluorinated group such as $-(CF_2)_n-CH_3$, $-(CF_2)_n-CF_3$, $-\phi F_{1-6}$, and

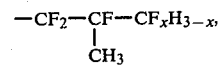

where $\phi$ is phenyl, n is an integer from 1 to about 8, and x is an integer from 1 to 3.

In addition to the use of only fluorine-containing monomer(s) and/or oligomer(s), the polymerizable prepolymer system may comprise mixtures of a non-fluorinated monomer(s) and/or oligomer(s) with a fluorine-containing monomer(s) and/or oligomer(s), provided that the solubility parameters allow mutual solubility before and after polymerization. Examples of non-fluorine containing monomers and oligomers which may be used include:
Bisphenol A-bis ethyl methacrylate
Bisphenol A-bis propyl methacrylate
Bisphenol A-bis isopropyl methacrylate and higher analogues, and
Methyl methacrylate
Vinyl toluene
Styrene
Alkyl methacrylate When the binder system comprises a particulate, hydrophobic fluorine-containing polymer the particulate polymer may comprise a homopolymer, for example, of a fluorocarbon acrylate or methacrylate, or a copolymer prepared from such acrylates and methacrylates. Accordingly, monomers suitable for preparing a fluorine-containing polymers include, for example, heptafluorobutyl acrylate and methacrylate, hexafluoroisopropyl acrylate and methacrylate, pentafluoropropyl acrylate and methacrylate, trifluorethyl acrylate and methacrylate, octafluoropentyl acrylate and methacrylate, and vinyl fluoride. The particulate fluorine-containing polymers may also include copolymers prepared from any fluoroalkyl acrylate or methacrylate monomer, vinyl fluoride, and a non-fluorinated monomer, such as, for example, glycidyl methacrylate, hydroxyethyl methacrylate, an alkyl acrylate or methacrylate, or a vinyl aromatic compound such as p-vinyl phenol. The homopolymerization of fluorinated acrylates and methacrylates and the copolymerization of a fluorinated monomer, for example, hexafluorobutyl methacrylate, and a non-fluorinated monomer, for example, p-vinyl phenol is described in Overberger and Sincich, *Journal of Polymer Science*, A-1 13:1782–1792, 1975. In that article, it is noted that the homopolymerization and copolymerization reactions can be performed in bulk using azobisisobutyronitrile as the initiator in sealed tubes. The reactions can be carried out in an oil bath at about 65°–80° C. for about 16–18 hours. Although, as pointed out above, a wide variety of fluorocarbons may be incorporated as the hydrophobic portion of the present dental compositions, the methacrylate analogues have been found to be preferred. It has also been found preferable to reduce the bulk fluorine-containing polymer to a powder ranging in particle size of from about 10 to 500 $\mu$m, before its incorporation into the present compositions.

The particulate fluorine-containing polymer preferably is employed as a dispersion in a polymerizable prepolymer system, and generally is present in an amount of from about 5 to 80% by weight of the total dental composition. The polymerizable prepolymer system in which the particulate fluorine-containing polymer may be incorporated may comprise any of the acrylate prepolymers conventionally employed in dental resins. However, since it is an object of the present invention to provide dental restoratives which are hydrophobic such that the sum of the free surface energy changes as a result of saliva wetting the tooth and the restorative is positive, it is preferred to employ prepolymers which are hydrophobic or only minimally hydrophilic. Accordingly, it is preferred to disperse the particulate fluorine-containing polymer in a fluorine-containing prepolymer system of the above described type. Thus, among the prepolymers which are most suitable for use herein are included: fluoro monomers, such as
    tetrafluoropropyl methacrylate,
    pentafluorophenyl methacrylate,
    hexafluorohexyl methacrylate,
    hexafluoroisopropyl methacrylate, and
    octafluoropentyl methacrylate;
dimethacrylates, such as
    fluorinated analogues of mono-, di-, tri-, and tetra-ethylene glycol dimethacrylates;
aromatic dimethacrylates, such as
(1) Bisphenol A adducts of methacrylates in which alkyl groups are fluorinated,
(2) Bisphenol A adducts in which aromatic groups are fluorinated, and
(3) Bisphenol A adducts of methacrylates in which the aromatic and methacrylate groups are fluorinated.

Other unsaturated molecules which can be used include for example
    fluorovinyl toluene,
    fluorostyrene, and
    fluoroalkyl methacrylate, as well as fluorinated acrylates of the following types:

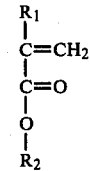

where $R_1$ is a $C_1$–$C_4$ alkyl group and $R_2$ is a fluorinated group such as $(CF_2)_n$—$CH_3$, —$(CF_2)_n$—$CF_3$, —$\phi F_{1-6}$, and

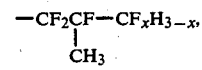

where $\phi$ is phenyl, n is an integer from 1 to about 8, and x is an integer from 1 to 3.

As noted above, the polymerizable prepolymer system in which the particulate fluorine-containing polymer is dispersed may include non-fluorinated analogues of the above acrylate prepolymers in addition to or in place of the fluorinated prepolymers, so long as the final binder system is hydrophobic.

The compositions employed in the present process, as noted above, contain at least about 10% by weight and up to about 90% by weight, and preferably about 70–80% by weight of a finely divided, inert inorganic filler. The filler, which may be in the form of spheres, platelets, fibers, whiskers, or particles of any regular or irregular shape and which preferably is transparent or translucent, may comprise for example, apatite, soda glass, barium glass, borosilicate glass, silica, alumina, quartz, lithium aluminum silicate or the like. Mixtures of more than one filler may be used. The particle size of the filler may range from about 0.005 to about 0.5 $\mu$m in the case of microfine silica, to not greater than about 500 $\mu$m in the case of irregularly shaped particles. Further, a range of particle sizes may be used. Where the filler is in the form of fibers, the maximum dimension of the fibers preferably is not greater than about 110 $\mu$m. On the other hand, where the filler is in the form of spheres, platelets or is irregularly shaped, the maximum dimension of the particles preferably is not greater than about 350 $\mu$m. The filler should have a Knoop hardness of at least about 300 kg/mm$^2$ and up to about 2000 kg/mm$^2$ for alumina, and preferably about 400–600 kg/mm$^2$. In addition, it is preferred that the filler be treated with a keying or coupling agent to improve the binding of the parent resin thereto. The keying agents described in U.S. Pat. No. 3,066,112 to Bowen are well suited for this purpose, although other keying agents suitable to the present resins may be used. Those agents found to be particularly suitable include the silanes, such as $\alpha$-acrylpropoxy triethoxy silane, $\alpha$-methacryloxypropyltrimethoxysilane, vinyltriacetoxysilane, vinyltris(2-methoxyethoxy) silane, allyltrichlorosilane, allyetrialkylsilanes, allyldialkylsilanes or diphenyl vinyl ethoxysilane; and the fluorosilanes, such as hydrooctafluorobutyltrichlorosilane; 1,1,2,2-tetrafluoroethylmethyldichlorosilane; 1,1,2,2-tetrafluoroethyltrichlorosilane, or (3,3,3-trifluoropropyl) trichlorosilane. The use of fluorosilanes is particularly advantageous since the fluorosilanes enhance the hydrophobicity of the set composite. Vinyl substitution as well as fluorine substitution in the silane coupler will maintain strength as well as hydrophobicity of the set composite.

The dental compositions used in the present invention may be formulated into one or two package systems for convenient handling and working. For example, the compositions may be formulated in a two-paste system in which one paste contains a free radical initiator, such as benzoyl peroxide, cumene hydroperoxide, or inorganic peroxides (present from 0.01–5.0% by weight), together with a portion of the filler and fluorine-containing polymerizable prepolymer system, and other paste contains a tertiary amine such as N,N-dimethyl paratoluidine, N,N-dihydroxyethyl p-toluidine (0.01–5.0% by weight), together with the balance of the filler and prepolymer system.

In the alternative, a one-paste system may be used wherein ultraviolet light is used to initiate setting. Such a system would include, for example, benzoin or one of its ethers (0.01–5.0% by weight) as the active constituent. A one-phase system which is initiated by visible light also could be formulated. In such a system the active constituents would comprise, for example, a α-diketone (0.01–1.0% by weight), such as camphoroquinone, benzil, or biacetyl, and an amine reducing agent (0.01–1.0% by weight), such as dimethylaminoethyl methacrylate, or trialkylamine, or 1,4-bismethylene N,N-dialkyl benzene. The compositions may also be formulated as a two-part system in which the first part is almost entirely inorganic filler and the second part is almost entirely polymerizable prepolymer. In this way the filler/prepolymer ratio can be controlled at the discretion of the operator, who may then use the composite in as thin a consistency as to constitute a varnish. The invention is illustrated by the following examples:

EXAMPLE 1

Fused quartz sand was ground in a porcelain ball mill to a size that passed through a 200 mesh screen. 500 gms. of this ground quartz were placed in 1000 ml. of 20% hydrochloric acid and heated to 80° C. for 1 hour. The acid was filtered off and the pigment washed with water until the effluent reached a pH of 6 to 7. The pigment was dried in an open glass tray at 130° C. A water solution of silane was prepared by placing 0.4 ml. acetic acid and 10 gms. of trimethoxysilylpropyl methacrylate in 200 gms. of water and stirring rapidly at room temperature. A slurry was prepared of the pigment and the silane solution. The slurry was placed in a glass tray and evaporated to dryness at 130° C. The mixture was stirred frequently during the drying process. 75.52 parts by weight of the above silanated fused quartz were added using slow speed high torque revolutions to a clear solution comprised of 18.52 parts by weight octafluoropentylmethacrylate, 6.17 parts by weight Diacryl 101 (70% Bisphenol A-bis ethyl methacrylate, marketed by Akzo Chemie b.v., Amensfoot, Holland), 0.19 parts by weight camphoroquinone and 0.12 parts by weight N,N-dimethylamino ethyl methacrylate. The resulting single paste was polymerized by blue light from a projector bulb with a 12 V and 100 W rating. The formula of the polymerizable composition is set forth on Table 1, whereas the physical properties of the polymerized product are set forth in Table 2.

TABLE 1

| Components of polymerizable compositions | % by weight |
| --- | --- |
| Octafluoropentylmethacrylate | 18.52 |
| Diacryl 101[a] | 6.17 |
| Silanated quartz | 75.52 |
| Camphoroquinone | 0.19 |
| N,N-dimethylamino ethyl methacrylate | 0.12 |

[a]Akzo Chemie b.v., Amensfoot, Holland.

TABLE 2

| Properties of Polymerized Composition | Value |
| --- | --- |
| Indentation Depth, mm | 0.065 (0.001)[a] |
| Recovery, % | 66.1 (1.5) |
| Compressive Strength, MPa | 127 (2.9) |
| 0.1% Yield Strength, MPa | 80 (4.8) |
| Modulus of Elasticity, MPa × $10^4$ | 1.50 (0.11) |
| Tensile Strength, MPa | 29.0 (1.2) |
| Abrasive Wear, $mm^3$/mm × $10^{-4}$ | 8.0 (0.2) |
| Inorganic Phase, weight % | 76.2 (0.2) |
| Working Time, min. | 35 seconds |
| Free Polymerization Contraction, Vol. % | 3.1 (0.3) |
| Density, g/cc | 2.16 (0.03) |
| Thermal Coefficient of Expansion, /°C. × $10^{-6}$ | 55.7 (5.0) (0–60° C.) |
| Water Sorption (mg/$cm^2$) | |
| 24 hours | 0.09 (0.01) |
| 48 hours | 0.13 (0.01) |
| 7 days | 0.14 (0.01) |
| 14 days | 0.15 (0.02) |
| Solubility, % | |
| 14 days | <0.01 |
| Contact angle[b], Advancing (θA) deg. | 156 (1.3) finished |

[a]Values in parentheses are standard deviations.
[b]The "finished" contact angle was measured after the polymerized composition was buffed with a standard 600 mesh SiC metallographic paper.

EXAMPLE 2

In this example, the constituents, percentages, and procedure were in Example 1, except that the octafluoropentylmethacrylate was partially polymerized to the consistency of a mobile syrup before it was mixed with the other constituents. This partial polymerization was accomplished with a tungsten lamp (100 watt and 12 volts) over a period of one-half hour with stirring. This syrup was then used to formulate the composite as in Example 1. This procedure resulted in composites exhibiting essentially the same contact angle with water and essentially the same physical properties outlined in Table 2, except that the gel time (working time) was shortened to 10–15 seconds.

EXAMPLE 3

The constituents, percentages and procedure of Example 1 was repeated, except that polymerization was not initiated by camphoroquinone and N,N-dimethylamino ethyl methacrylate in the presence of blue light. Rather the paste consisting of octafluoropentylmethacrylate, Diacryl 101, and silanated quartz was divided into two equal parts. Benzoyl peroxide (0.32%) was added to one part and N,N-dimethyl-p-toluidine (0.28%) was added to the second part. Equal quantities of the two pastes were spatulated and the setting time of the mix was 2.6 minutes. The physical and mechanical properties were essentially the same as for Example 1, except that the contact angle with water was 4° higher, i.e., 160°.

In controlled experiments with commercially available composites, the composite of the above Example 1 stained less on visual examination after soaking in anionic and cationic dyes and in such biological stains as tea and coffee.

Further, in presence of a marginal defect of 0.001 inch a composite filling prepared from the composition of the Example 1 in an extracted tooth did not spontaneously leak; but required a pressure of water 2 cm. high before obvious penetration occurred. In contrast composite fillings of commercially available materials leaked spontaneously under similar conditions.

Controlled experiments with cavity preparations in extracted teeth have shown, using scanning electron microscopy, that the mixed composite is sufficiently plastic to penetrate the acid etched enamel surfaces of the cavity preparation under digital pressure and ambient conditions forming tags that provide mechanical retention of the material.

Having described an invention with particular reference to precise examples thereof, it is to be understood that the invention is not limited to those examples, and that various modifications and changes may be made by one skilled in the art without departing from the scope or spirit of the invention.

We claim:

1. In a process for treating a tooth, the steps comprising applying a polymerizable dental composition to a surface of the tooth, said composition comprising a mixture of from about 10 to about 90% by weight of a finely divided, inert organic filler and from about 90 to about 10% by weight of at least one polymerizable fluorine-containing prepolymer selected from the group consisting of perfluoroalkyl acrylates, aromatic diacrylates containing ring substituted fluorine, fluorinated acrylates of the formula

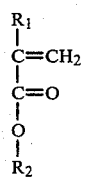

where $R_1$ is a $C_1$-$C_4$ alkyl group, $R_2$ is a fluorinated group selected from $-(CF_2)_n-CH_3$, $-(CF_2)_3$, $-\phi F_{1-6}$, and

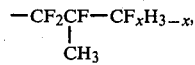

where $\phi$ is phenyl, n is an integer from 1 to about 8 and x is an integer from 1 to 3, and fluorinated analogues of aliphatic diacrylates and mixtures thereof; and polymerizing said composition on the tooth surface, said composition, when polymerized, (1) being hydrophobic such that the sum of the free surface energy changes as a result of saliva wetting the tooth surface and said polymerized composition is positive and (2) exhibiting an advancing contact angle in relation to water of at least 130°.

2. In a process for treating a tooth, the steps comprising applying a polymerizable dental composition to a surface of the tooth, said composition comprising a mixture of from about 10 to about 90% by weight of a finely divided inert organic filler and from about 90 to about 10% by weight of at least one polymerizable fluorine-containing prepolymer selected from the group consisting of perfluoroalkyl acrylates, aromatic diacrylates containing ring substituted fluorine, fluorinated acrylates of the formula

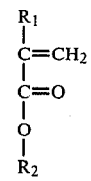

where $R_1$ is a $C_1$-$C_4$ alkyl group, $R_2$ is a fluorinated group selected from $-(CF_2)_n-CH_3$, $-(CF_2)_3$, $-\phi F_{1-6}$, and $-CF_2CF-CF_xH_{3-x}$, where $\phi$ is phenyl, n is an integer from 1 to about 8, and x is an integer from 1 to 3, and fluorinated analogues of aliphatic diacrylates and mixtures thereof; and polymerizing said composition on the tooth surface, said composition, when polymerized, exhibiting an advancing contact angle in relation to water of at least 130°.

3. The process of claim 1 wherein all of the fluorine-containing prepolymers, when more than one prepolymer is employed, are mutually soluble before and after polymerization.

4. The process of claim 2 wherein all of the fluorine-containing prepolymers, when more than one prepolymer is employed, are mutually soluble before and after polymerization.

5. The process of claim 2 wherein said fluorine-containing prepolymer comprises a perfluoroalkyl acrylate.

6. The process of claim 2 wherein said fluorine-containing prepolymer comprises an aromatic diacrylate containing ring substituted fluorine.

7. The process of claim 2 wherein said fluorine-containing prepolymer comprises a fluorinated acrylate of the formula:

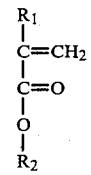

where $R_1$ is a $C_1$-$C_4$ alkyl group, $R_2$ is a fluorinated group selected from $-(CF_2)_n-CH_3$, $-(CF_2)_3$, $-\phi F_{1-6}$, and

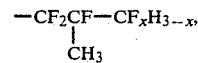

$\phi$ is the phenyl radical, n is an integer from 1 to about 8, and x is an integer from 1 to 3.

8. The process of claim 2 wherein said fluorine-containing prepolymer comprises a fluorinated analogue of an aliphatic diacrylate.

9. The process of claim 1 in which said tooth surface is the surface of a tooth cavity.

10. The process of claim 2 in which said tooth surface is the surface of a tooth cavity.

* * * * *

UNITED STATES PATENT AND TRADEMARK OFFICE
CERTIFICATE OF CORRECTION

PATENT NO. : 4,292,029
DATED : September 29, 1981
INVENTOR(S) : Robert G. Craig, et al It is certified that error appears in the above—identified patent and that said Letters Patent is hereby corrected as shown below:

On the Title page in the list of references, "Nitzackel et al." should read -- Nitzsche et al. --.

"Sheerniss et al." should read -- Sheerness et al. --.

"Beech (J. Demt. Res., 51:1438-1442, 1972)." should read -- Beech (J. Dent. Res., 51:1438-1442, 1972).--.

Column 1, lines 40, 50, 56, 65 and 68 (each occurrence), the name "Chaug et al." should read -- Chang et al.--.

Column 6, line 65, "allyetrialkylsilanes" should read -- allyltrialkylsilanes --.

Column 9, line 28, "organic" should read -- inorganic --.

Column 9, line 65, "organic" should read -- inorganic --.

Column 10, line 16, the formula "$-CF_2CF-CF_xH_{3-x}$" should read $$-CF_2\underset{\underset{CH_3}{|}}{C}F-CF_xH_{3-x}$$

Signed and Sealed this

Twenty-third Day of February 1982

[SEAL]

Attest:

GERALD J. MOSSINGHOFF

*Attesting Officer*   *Commissioner of Patents and Trademarks*